(12) United States Patent
Shimagami et al.

(10) Patent No.: US 8,669,287 B2
(45) Date of Patent: Mar. 11, 2014

(54) EMULSIFYING PREPARATION

(75) Inventors: Yoko Shimagami, Kanagawa (JP);
Yasushi Ichimi, Mie (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/311,074

(22) Filed: Dec. 5, 2011

(65) Prior Publication Data
US 2012/0142774 A1   Jun. 7, 2012

Related U.S. Application Data

(63) Continuation of application No. PCT/JP2010/059555, filed on Jun. 4, 2010.

(30) Foreign Application Priority Data

Jun. 5, 2009 (JP) .................................. 2009-136262

(51) Int. Cl.
*A01N 37/06* (2006.01)
*A61K 31/22* (2006.01)
*A23D 7/00* (2006.01)
*A23D 7/06* (2006.01)

(52) U.S. Cl.
USPC ........................... 514/549; 426/602; 426/604

(58) Field of Classification Search
USPC .......................................... 426/602; 514/549
See application file for complete search history.

(56) References Cited

U.S. PATENT DOCUMENTS

| | | | |
|---|---|---|---|
| 5,162,377 A | 11/1992 | Kakoki et al. | |
| 5,709,895 A | 1/1998 | Tanaka et al. | |
| 6,005,126 A * | 12/1999 | Ishitobi et al. | 554/227 |
| 6,303,662 B1 | 10/2001 | Nagahama et al. | |
| 6,620,904 B2 * | 9/2003 | Lemke | 528/295.5 |
| 2004/0115161 A1 * | 6/2004 | Oyama et al. | 424/70.31 |
| 2005/0069579 A1 | 3/2005 | Kamaguchi et al. | |
| 2006/0147515 A1 | 7/2006 | Liu et al. | |
| 2006/0287390 A1 * | 12/2006 | Sagawa et al. | 514/546 |
| 2007/0141165 A1 | 6/2007 | Takakura et al. | |
| 2007/0248631 A1 * | 10/2007 | Takase et al. | 424/401 |
| 2007/0264411 A1 * | 11/2007 | Ito et al. | 426/602 |
| 2008/0131515 A1 * | 6/2008 | Ogawa et al. | 424/489 |
| 2009/0018358 A1 | 1/2009 | Kondo et al. | |

FOREIGN PATENT DOCUMENTS

| | | | |
|---|---|---|---|
| EP | 0 659 347 | 6/1995 | |
| EP | 0 913 191 | 5/1999 | |
| EP | 1 902 633 | 3/2008 | |
| EP | 1 927 287 | 6/2008 | |
| JP | 61-260860 | 11/1986 | |
| JP | 7-184544 | 7/1995 | |
| JP | 09-168369 | 6/1997 | |
| JP | 10-84887 | 4/1998 | |
| JP | 11-49664 | 2/1999 | |
| JP | 11-236330 | 8/1999 | |
| JP | 2000-312598 | 11/2000 | |
| JP | 2002/78650 | 10/2002 | |
| JP | 2003-192576 | * 7/2003 | ............. A61K 9/107 |
| JP | 2007-267683 | 10/2007 | |
| JP | 2007-269714 | 10/2007 | |
| JP | 2007-277181 | 10/2007 | |
| JP | 2007-289074 | 11/2007 | |
| JP | 2008-63476 | 3/2008 | |
| JP | 2009-95253 | 5/2009 | |
| JP | 2011-120604 | 6/2011 | |
| JP | 2011-132176 | 7/2011 | |
| JP | 2011-168527 | 9/2011 | |
| WO | 2007/114128 | 10/2007 | |

OTHER PUBLICATIONS

Sutoh, K., J. Agric. Food Chem. vol. 49, 4026-4030. Published 2001.*
International Search Report issued in PCT/JP2010/059555 on Jun. 29, 2010.
K. Kobata et al., Biosci. Biotechnol. Biochem, vol. 66 No. 2 (2002) pp. 319-327.
E. Dickinson, "An Introduction to Food colloids", pp. 47-50 (1992).
S. Pinnamaneni et al., Pharmazie, vol. 58 (2003), pp. 554-558.
W. P. Oliveira et al., Journal of Dispersion Science and Technology. vol. 26 (2005) pp. 243-249.
Supplementary European Search Report issued Dec. 3, 2013, in Patent Application No. 10783468.1

* cited by examiner

*Primary Examiner* — Paul Zarek
*Assistant Examiner* — George W Kosturko
(74) *Attorney, Agent, or Firm* — Oblon, Spivak, McClelland, Maier & Neustadt, L.L.P.

(57) ABSTRACT

An emulsifying preparation for an oil-soluble component, which is sensorily superior when applied to an aqueous phase, can maintain stability for a long time, and imposes less restriction for formulation or production is provided. The emulsifying preparation of the present invention contains (A) an oil phase component containing an oil-soluble component, (B) an aqueous phase component containing a polyol, and (C) an emulsifier containing polyglycerol fatty acid monoester having an average degree of polymerization of not less than 10, and having an HLB value of not less than 14 and not more than 18 or showing a transmittance of 1 wt % aqueous solution at 600 nm of not less than 80%.

14 Claims, 1 Drawing Sheet

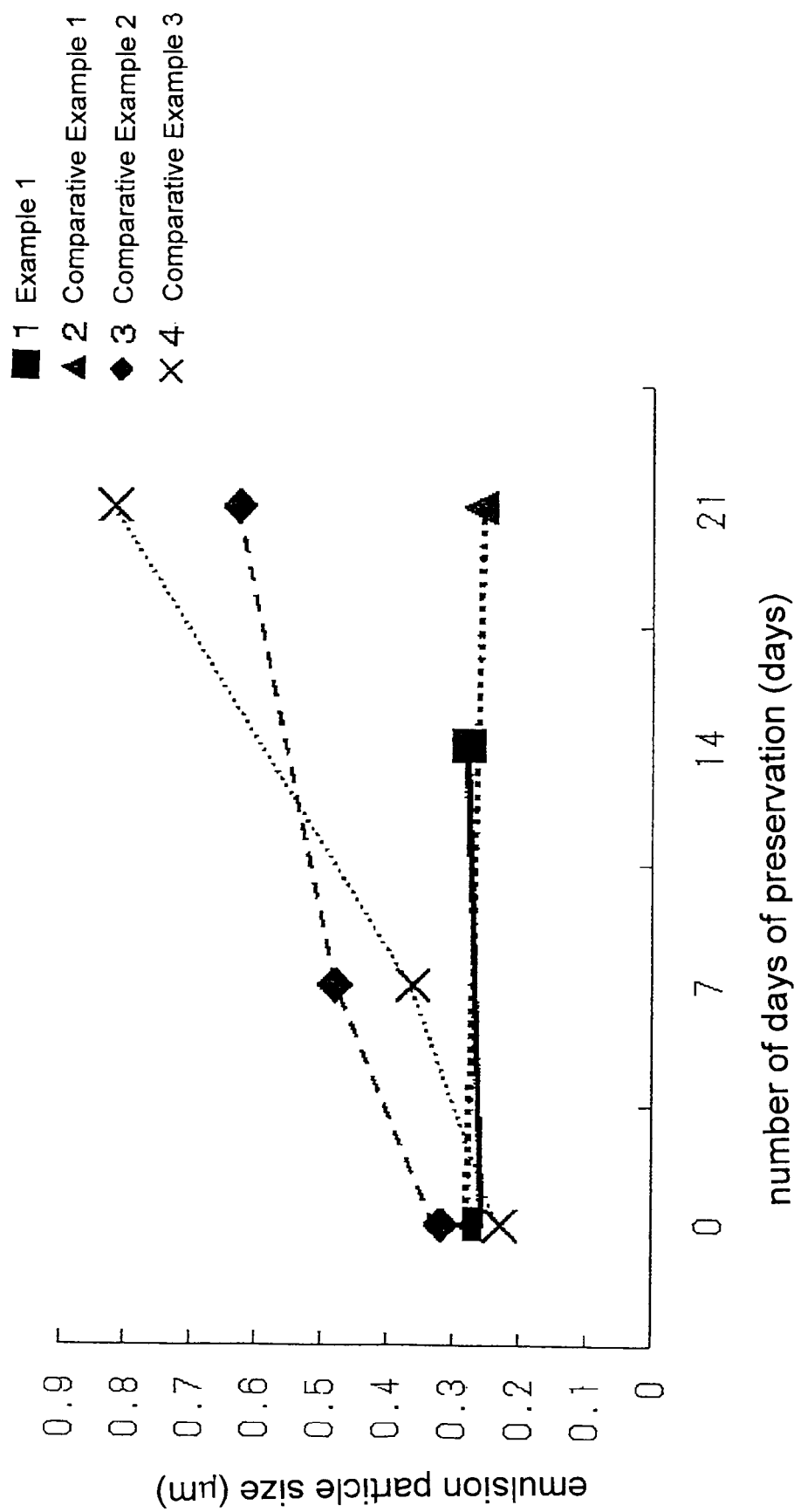

EMULSIFYING PREPARATION

CROSS REFERENCES TO RELATED APPLICATIONS

This application is a continuation of International Patent Application No. PCT/JP2010/059555, filed on Jun. 4, 2010, and claims priority to Japanese Patent Application No. 2009-136262, filed on Jun. 5, 2009, both of which are incorporated herein by reference in their entireties.

BACKGROUND OF THE INVENTION

1. Field of the Invention

The present invention relates to emulsifying preparations which contain an oil-soluble active ingredient, which is superior in long-term preservation stability.

2. Discussion of the Background

Conventionally, a number of oil-soluble drugs as well as oil-soluble components such as oil-soluble vitamins, dyes, flavors, plant essential oils, and the like are known as active ingredients to be added to pharmaceutical products, foods and the like. These oil-soluble components can be dissolved in oil and provided in the form of a capsule. For wide utilization in pharmaceutical products such as liquid and the like, foods such as drinks and the like, the use of an aqueous phase system is desired to be enabled.

To contain an oil-soluble component in an aqueous phase, therefore, various solubilization, dispersion, and emulsification techniques have been considered. For example, there are: a technique in which ultrafine crystals of an oil-soluble dye are dispersed in a mixture of polyglycerol fatty acid ester having the below-mentioned HLB value of 10-15, sorbitan ester of fatty acid having an HLB value of 2-6 and/or diglycerol fatty acid ester having an HLB value of 2-6, polyols and water (see JP-A-2008-63476); a method in which a polyglycerol fatty acid monoester made of a polyglycerol having an average degree of polymerization of not less than 5 and myristic acid or oleic acid monoester, and polyol are mixed at a particular ratio and a homogeneous treatment is performed (see JP-A-H10-84887); a technique in which a polyglycerol fatty acid monoester made of polyglycerol having an average degree of polymerization of 6-10 and saturated fatty acid having a carbon number of 12-14, and fats and oils are mixed at a particular ratio to solubilize the fats and oils (see patent document 3: JP-A-H9-168369); and the like. In addition, a technique in which the pH of emulsifying preparations containing capsinoid compounds in chili pepper containing various physiologically active components is set to fall within a particular range has been disclosed (see JP-A-2003-192576).

The emulsifying preparations shown in the above-mentioned patent documents were those prepared by using a polyglycerol fatty acid ester produced by a conventional production method. In the polyglycerol fatty acid ester produced by a conventional production method here, the polyglycerol used as a starting material is generally obtained by dehydrative condensation of glycerol as a starting material in the presence of a catalyst such as sodium hydroxide and the like under heating, followed by purification as necessary by distillation, decoloration, deodorizing, ion exchange resin treatment, and the like.

The polyglycerol produced by such steps is a mixture of dehydratively-condensed compounds of glycerol having different structures. This is because the molecular structure of polyglycerol produced varies depending on which hydroxyl group is involved in the reaction during the condensation of glycerols, since glycerol has two primary hydroxyl groups and one secondary hydroxyl group. The structure of polyglycerol has a great influence on the properties of polyglycerol fatty acid ester. Conventional polyglycerol esters of fatty acid are not designed in consideration of the structure of a hydrophilic group to meet the use object, and therefore, the properties thereof are not sufficiently exhibited. Although the information reflecting the molecular structure of polyglycerol can be obtained by various methods, determination of a rigorous molecular structure is meaningless since it is a mixture as mentioned above. However, it is possible to increase the molecular species having a certain tendency by combining synthesis methods and purification methods, even if it is a mixture.

In general, with regard to polyglycerol, for example, decaglycerol refers to polyglycerol having a degree of polymerization of 10. However, those actually commercially available include many polyglycerols having a degree of polymerization of other than 10, and they are mixtures of polyglycerols having various degrees of polymerization. As a method of determining the average degree of polymerization of polyglycerol, an end-group analysis method is generally used, which determines by calculation from the relationship between a measurement value of hydroxyl value and a theoretical value thereof. Therefore, conventional polyglycerol is, even if it is a decaglycerol, characterized in that it contains decaglycerol having a degree of polymerization of 9 or 10 in a comparatively small amount, and instead, decaglycerol having a low degree of polymerization in a large amount, where the total of decaglycerol having a degree of polymerization of not less than 6 is less than 65 wt %, the total of decaglycerol having a degree of polymerization of not less than 7 is less than 60 wt %, and the total of decaglycerol having a degree of polymerization of not less than 8 is less than 50 wt %. Moreover, the total of polyglycerol produced by a conventional method and having a linear or branched chain structure is less than 60 wt %. The rest mostly has a cyclic structure. A conventional production method cannot determine which hydroxyl group reacts during condensation of glycerols, and also produces many cyclic polyglycerols. When compared to polyglycerol having a linear or branched chain structure, polyglycerol having a cyclic structure contains less hydroxyl group, which decreases hydrophilicity, and cannot maintain emulsification stability easily for a long time since the cyclic structure becomes an inhibitory factor for emulsification. Therefore, an ester of polyglycerol produced by a conventional production method and fatty acid cannot retain high emulsification performance and high solubilization performance and cannot maintain a stable emulsification state for a long time.

Examples of the surfactants for foods currently available on the market include sucrose esters of fatty acid, polyoxyethylene sorbitan fatty acid esters, and the like. When drinks containing a liposoluble vitamin such as vitamin E and the like, and an oil-soluble useful substance such as β-carotene and the like are produced using such surfactant having a high HLB value, a product that is stable for a long time cannot be produced. As a result, an auxiliary agent such as ethanol and the like needs to be added to achieve sufficient and stable emulsification performance. However, when such drinks are taken in a large amount, drunkenness occurs, sometimes causing a social problem particularly among young people. That is, by a technique using a conventional polyglycerol fatty acid ester, it is difficult to provide a stable emulsified state superior in sensory aspects such as taste, texture, and the like, since emulsification performance is insufficient. In addition, the polyoxyethylene sorbitan fatty acid esters and sucrose esters of fatty acid widely used as surfactants for foods show insufficient emulsification and solubilization performances, and cannot be sufficient substitutes.

Considering the application to pharmaceutical products and foods, moreover, it is preferable in terms of sensory aspects such as taste, texture, and the like to add higher amounts of oil-soluble components or oil phase components desired to be added to an emulsifying preparation and to decrease the amount of the emulsifying preparation itself to be added to pharmaceutical products such as liquid and the like and foods such as drinks and the like, since the amounts of a solubilizer, a dispersing agent, and an emulsifier to be ingested become small. When an emulsifying preparation is applied to liquid pharmaceutical products such as liquids and the like or liquid foods such as drinks and the like, it is necessary to maintain a stable, solubilized, dispersion or emulsified state for a long time without creaming, oil phase separation, and the like. For this end, it is desirable to maintain a good emulsified state during the use period or best-before period of the emulsifying preparation.

SUMMARY OF THE INVENTION

Accordingly, it is one object of the present invention to provide novel preparations for emulsifying an oil-soluble component.

It is another object of the present invention to provide novel preparations for emulsifying an oil-soluble component, which are sensorily superior even when added to pharmaceutical products such as liquids and the like and foods such as drinks and the like, which can maintain stability for a long time, and which impose fewer restrictions for formulation or production These and other objects, which will become apparent during the following detailed description, have been achieved by the inventors' discovery that an emulsifying preparation comprising (A) an oil phase component comprising an oil-soluble component, (B) an aqueous phase component comprising a polyol and, as an emulsifier, (C) an emulsifier comprising polyglycerol fatty acid monoester having an average degree of polymerization of not less than 10 and having certain properties is sensorily superior even when added to pharmaceutical products such as liquids and the like and foods such as drinks and the like and can maintain good preservation stability for a long time.

Accordingly, the present invention provides:

(1) An emulsifying preparation, comprising:

(A) an oil phase component comprising an oil-soluble component;

(B) an aqueous phase component comprising a polyol; and (C) an emulsifier comprising polyglycerol fatty acid monoester having an average degree of polymerization of not less than 10 and having an HLB value of not less than 14 and not more than 18.

(2) An emulsifying preparation, comprising:

(A) an oil phase component comprising an oil-soluble component;

(B) an aqueous phase component comprising a polyol; and (C) an emulsifier comprising polyglycerol fatty acid monoester having an average degree of polymerization of not less than 10 and showing a transmittance of 1 wt % aqueous solution at 600 nm of not less than 80%.

(3) The emulsifying preparation of the above-mentioned (1) or (2), wherein (A) the oil phase component comprising an oil-soluble component is contained in an amount of 20 to 50 wt % of the total amount of the emulsifying preparation.

(4) The emulsifying preparation of any of the above-mentioned (1)-(3), wherein (B) the aqueous phase component comprising a polyol is contained in an amount of 20 to 79.9 wt % of the total amount of the emulsifying preparation.

(5) The emulsifying preparation of any of the above-mentioned (1)-(4), wherein (C) the emulsifier is contained in an amount of 0.1 to 30 wt % of the total amount of the emulsifying preparation.

(6) The emulsifying preparation of any of the above-mentioned (1)-(4), wherein (C) the emulsifier comprises polyglycerol monooleate or monomyristate having an average degree of polymerization of not less than 10.

(7) The emulsifying preparation of any of the above-mentioned (1)-(6), wherein (C) the emulsifier comprises polyglycerol fatty acid monoester having an average degree of polymerization of not less than 10, wherein the content of polyglycerol having a degree of polymerization of not less than 6 is not less than 65 wt % in total.

(8) The emulsifying preparation of any of the above-mentioned (1)-(7), wherein (C) the emulsifier comprises polyglycerol fatty acid monoester having an average degree of polymerization of not less than 10, and comprising linear or branched chained polyglycerol in an amount of not less than 60 wt % in total.

(9) The emulsifying preparation of any of the above-mentioned (1)-(8), wherein the oil-soluble component contained in (A) the oil phase component is a capsinoid compound.

(10) The emulsifying preparation of the above-mentioned (9), wherein the capsinoid compound is one or more kinds selected from the group consisting of capsiate, dihydrocapsiate and nordihydrocapsiate.

The emulsifying preparation of the present invention is sensorily superior even when added to pharmaceutical products such as liquids and the like and foods such as drinks and the like, can maintain good preservation stability for a long time, and is suitable for applying an oil-soluble component to an aqueous phase.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows the preservation stabilities of the emulsifying preparations of Example 1 and Comparative Examples 1-3 at 5° C. Explanation of symbols: ■1, Example 1; ▲2, Comparative Example 1; ♦3, Comparative Example 2; and X4, Comparative Example 3.

DETAILED DESCRIPTION OF THE PREFERRED EMBODIMENTS

In the emulsifying preparation of the present invention, as the oil phase component of (A), fats and oils used for pharmaceutical products and foods can be used. Examples thereof include hydrocarbon oils such as liquid paraffin, squalane, and the like; plant-derived fats and oils such as avocado oil, soybean oil, rape seed oil, palm oil, rice oil, corn oil, palm oil, safflower oil, olive oil, and the like; animal-derived fats and oils such as beef tallow, lard, chicken fat, fish oil, and the like; fatty acid diglycerides or triglycerides such as medium-chain saturated fatty acid diglyceride or triglyceride and the like; ester oils such as octyldodecyl myristate, sucrose fatty acid isobutyrate, and the like; and the like. One or more kinds thereof can be selected and used.

The oil phase component of the above-mentioned (A) can contain an oil-soluble active ingredient. Examples of the oil-soluble component include oil-soluble medicaments, oil-soluble vitamins such as liver oil, vitamin A, vitamin A oil, vitamin $D_3$, vitamin $B_2$ butyrate, natural vitamin E mixture, and the like; oil-soluble dyes such as paprika pigment, annatto pigment, tomato pigment, calendula pigment, β-carotene, astaxanthin, canthaxanthin, lycopene, chlorophyll, and the like; flavors such as peppermint oil, spearmint oil, cinnamon oil, and the like; plant essential oils such as limonene, linalool, nerol, citronellol, geraniol, citral, l-menthol, eugenol, cinnamicaldehyde, anethole, perillaldehyde, vanillin, γ-undecalactone, and the like; physiologically active components such as coenzyme $Q_{10}$, α-lipoic acid, conjugated linoleic acid, phytosterol, and the like; and the like. An amount effective for pharmaceutical products and foods can be added.

In the present invention, a capsinoid compound can be preferably used as the above-mentioned oil-soluble component. A capsinoid compound preferably refers to fatty acid ester of vanillyl alcohol, and representative components thereof include capsiate, dihydrocapsiate, nordihydrocapsiate confirmed as components contained in chili peppers, and further, also include fatty acid esters of various straight chain or branched chain fatty acid and vanillyl alcohol, which have a fatty acid chain length almost the same as capsiate and nordihydrocapsiate such as vanillyl decanoate, vanillyl nonanoate, vanillyl octanoate, and the like. Particularly, capsinoid compounds such as capsiate, dihydrocapsiate, nordihydrocapsiate, and the like, which are pungent-free components extracted from chili pepper, have been reported to have an immunostimulatory action, an energy metabolism activation action, and the like, and can be preferably used in the present invention.

Since capsinoid compounds are contained in large amounts in a plant body belonging to the genus Capsicum (hereinafter to be referred to as "chili pepper"), it can be prepared by purification and separation from a plant body and/or fruit of chili pepper. The chili pepper to be used for the purification is not particularly limited as long as it contains capsinoid, and a chili pepper derived from a native variety having a pungent taste represented by "NIKKO", "GOSHIKI", and the like may be used. However, a chili pepper of a pungent-free variety is preferable. Particularly, pungent-free varieties such as "CH-19 AMA", "MANGANJI", "FUSHIMIAMANAGA", and the like, green pepper, pepper and the like can be preferably used, since they contain a capsinoid compound in large amounts. Particularly, "CH-19 AMA", which is a pungent-free variety, is more preferable, since it has a high content of the component. In the present specification, the term "CH-19 AMA" means a group of varieties including "CH-19 AMA" variety, and progeny variety derived from "CH-19 AMA", and the like. Extraction, separation, and purification of the capsinoid compound can be performed by solvent extraction, various chromatographys such as silica gel chromatography and the like, high performance liquid chromatography for preparation and the like, which are well known to those of ordinary skill in the art, used singly or in appropriate combination. For example, the extraction method with ethyl acetate and described in JP-A-H11-246478, which is incorporated herein by reference, the extraction method with supercritical carbon dioxide or carbon dioxide nearby and described in JP-A-2002-226445, which is incorporated herein by reference, and the like can be mentioned.

In addition, the above-mentioned capsinoid compound can also be synthesized, for example, by a transesterification reaction using the corresponding fatty acid ester and vanillyl alcohol as starting materials as described in JP-A-H11-246478, which is incorporated herein by reference. It can also be synthesized based on the structural formula thereof by other reaction methods well known to those of ordinary skill in the art. Furthermore, it can also be prepared easily by a synthesis method using an enzyme. For example, by the method described in JP-A-2000-312598, Kobata et al. (Biosci. Biotechnol. Biochem., 66 (2), 319-327, 2002), both of which are incorporated herein by reference, a desired capsinoid compound can be easily obtained by utilizing a reverse reaction of lipase by using fatty acid ester corresponding to the desired compound and/or a compound such as triglyceride having a fatty acid and the like, and vanillyl alcohol as substrates.

When used for the preparation of the emulsifying preparation of the present invention, the capsinoid compound may be any of the above-mentioned extracts and synthesized products, and a single capsinoid compound may be used or a mixture of two or more kinds thereof may be used. Moreover, the capsinoid compound to be used may contain a decomposition product thereof (free fatty acid, vanillyl alcohol and the like).

Moreover, the oil phase of the above-mentioned (A) can contain, as long as the characteristics of the present invention are not impaired, one or more oil-soluble preservatives such as butyl p-hydroxybenzoate, dehydroacetic acid and the like, oil-soluble antioxidants such as dibutylhydroxytoluene (BHT), butylhydroxyanisole (BHA), rosemary extract, tocopherol acetate, stearyl ascorbate, γ-oryzanol, and the like, and the like. In the emulsifying preparation of the present invention, the oil phase of the above-mentioned (A) is preferably present in an amount of 20 to 50 wt % as a total oil phase component relative to the total amount of the emulsifying preparation.

In the emulsifying preparation of the present invention, the aqueous phase of (B) contains a polyol. Examples of the polyol include diols such as propanediol, 1,3-butanediol, hexanediol, and the like; triols such as glycerol and the like; sugar alcohols such as sorbitol, maltitol, reduction syrup, and the like; sugars such as glucose, sucrose, maltose, and the like; and the like. One or more kinds thereof can be selected and used.

The aqueous phase of the above-mentioned (B) can contain, as long as the characteristics of the present invention are not impaired, one or more inorganic salts such as potassium carbonate, sodium hydrogen carbonate, sodium carbonate, disodium dihydrogen pyrophosphate, and the like; inorganic acids such as phosphoric acid and the like and salts thereof; organic acids such as citric acid, adipic acid, succinic acid, tartaric acid, lactic acid, fumaric acid, malic acid, gluconic acid, gluconolactone, and the like and salts thereof; water-soluble vitamins such as vitamin $B_1$, vitamin $B_2$, vitamin $B_6$, ascorbic acid, and the like and salts thereof; water-soluble polymer compounds such as gum arabic, gum tragacanth, guar gum, xanthan gum, pectin, alginic acid and a salt thereof, carageenan, gelatin, casein, acrylic acid•methacrylic acid alkyl copolymer, cellulose derivatives such as hydroxyethylcellulose, carboxymethylcellulose, and the like, and the like; water-soluble preservatives such as sodium benzoate, methyl p-hydroxybenzoate and the like; and the like. The emulsifying preparation of the present invention preferably contains 20 to 79.9 wt % of the aqueous phase of the above-mentioned (B) as a total aqueous phase component relative to the total amount of the emulsifying preparation.

The emulsifying preparation of the present invention uses (C) an emulsifier comprising polyglycerol fatty acid monoester having an average degree of polymerization of not less than 10 and having certain properties.

The polyglycerol constituting the "polyglycerol fatty acid monoester having an average degree of polymerization of not less than 10" contained in (C) emulsifier preferably contains polyglycerol in which the content of polyglycerol having a degree of polymerization of not less than 6 is not less than 65 wt % in total and a large amount of polyglycerol having a high degree of polymerization. Moreover, polyglycerol containing linear polyglycerol and branched chain polyglycerol in not less than 60 wt % in total and having a small content of polyglycerol having a cyclic structure is preferable. The average degree of polymerization of polyglycerol is preferably not more than 30.

That is, as the polyglycerol constituting the "polyglycerol fatty acid monoester" contained in (C) emulsifier in the present invention, polyglycerol wherein the content of polyglycerol having a degree of polymerization of not less than 6 is not less than 65 wt % in total is preferably used. More preferably, polyglycerol wherein the content of polyglycerol having a degree of polymerization of not less than 6 is not less than 75 wt % in total is used, and further preferably, polyglycerol wherein the content of polyglycerol having a degree hydroxyl group. Since glycerols are fused in conventional production methods, a secondary hydroxyl group is involved in the reaction in many cases, and those having various molecular structures such as cyclic and the like are produced. By ring opening reaction of glycidol, linear or branched chain polyglycerol can be obtained with a high degree of polymerization distribution.

The degree of polymerization distribution of polyglycerol and the ratio of polyglycerol having a linear, branched chain, or cyclic structure can be measured by the following high-speed liquid chromatography mass spectrometer (LC/MS). The measurement conditions are as follows. The results of conventional decaglycerol are shown in Table 1, and those of decaglycerol preferably used in the present invention are shown in Table 2.

Aanalysis Conditions of LC/MS:
    ionization mode: APCI, negative
    measurement range: 90 to 2000
    column: TSK gel α-2500 (7.8×300 mm)
    temperature: 40° C.
    eluent: water/acetonitrile 7/3
    flow: 0.8 mL, 100 ppm
    analysis time: 20 minutes

TABLE 1

| | content (wt %) | | | | | | | | | | | | | | | | |
| --- | --- | --- | --- | --- | --- | --- | --- | --- | --- | --- | --- | --- | --- | --- | --- | --- | --- |
| | degree of polymerization | | | | | | | | | | | | | | | | |
| structure | 1 | 2 | 3 | 4 | 5 | 6 | 7 | 8 | 9 | 10 | 11 | 12 | 13 | 14 | 15 | 16 | total |
| chain | 2.1 | 3.5 | 4.7 | 6.3 | 7.3 | 6.3 | 6.1 | 4.9 | 4.3 | 3.7 | 2.3 | 1 | 0.2 | 0.1 | 0 | 0 | 52.8 |
| cyclic | 1.9 | 2.3 | 3.3 | 3.9 | 4.3 | 4.3 | 4.7 | 4.7 | 4.1 | 3.7 | 3.1 | 1.3 | 0.5 | 0.1 | 0 | 0 | 42.2 |
| unknown | | | | | | | | | | | | | | | | | 5 |

* In the Table, chain structure shows linear or branched chain structure.

TABLE 2

| | content (wt %) | | | | | | | | | | | | | | | | |
| --- | --- | --- | --- | --- | --- | --- | --- | --- | --- | --- | --- | --- | --- | --- | --- | --- | --- |
| | degree of polymerization | | | | | | | | | | | | | | | | |
| structure | 1 | 2 | 3 | 4 | 5 | 6 | 7 | 8 | 9 | 10 | 11 | 12 | 13 | 14 | 15 | 16 | total |
| chain | 0.8 | 1.8 | 2.4 | 3.7 | 5.7 | 7.3 | 8.8 | 10.8 | 12 | 11.3 | 8.4 | 5.6 | 3.7 | 2 | 0.8 | 0.2 | 85.3 |
| cyclic | 0 | 0 | 0.2 | 0.3 | 0.4 | 0.6 | 0.8 | 1.1 | 1.1 | 1.1 | 1.1 | 0.8 | 0.7 | 0.3 | 0.1 | 0 | 8.6 |
| unknown | | | | | | | | | | | | | | | | | 6.1 |

* In the Table, chain structure shows linear or branched chain structure.

of polymerization of not less than 6 is not less than 75 wt % in total, the content of polyglycerol having a degree of polymerization of not less than 7 is not less than 60 wt % in total, and the content of polyglycerol having a degree of polymerization of not less than 8 is not less than 50 wt % in total is used. The aforementioned polyglycerol preferably contains polyglycerol wherein the content of polyglycerol having a degree of polymerization of not less than 6 and not more than 30 is not less than 60 wt % in total. Moreover, polyglycerol containing linear polyglycerol and branched chain polyglycerol in not less than 60 wt % in total is preferably used, and polyglycerol containing linear polyglycerol and branched chain polyglycerol in not less than 80 wt % in total is more preferably used.

In the present invention, while the production method of polyglycerol of the "polyglycerol fatty acid monoester" contained in (C) emulsifier is not particularly limited, a method including synthesis using glycidol(2,3-epoxy-1-propanol) as a starting material, followed by purification is preferable. Glycerol has two primary hydroxyl groups and one secondary Examples of the "polyglycerol fatty acid monoester having an average degree of polymerization of not less than 10" include decaglyceryl monolaurate, decaglyceryl monomyristate, decaglyceryl monopalmate, decaglyceryl monostearate, decaglyceryl monooleate, and the like. One or more kinds thereof can be selected and used for the preparation of the emulsifying preparation of the present invention. The certain properties of the above-mentioned (C) emulsifier can be defined by the below-mentioned HLB value or transparency of an aqueous solution of the emulsifier.

First, in the present invention, as the above-mentioned (C) emulsifier having certain properties, one having the below-mentioned HLB value of not less than 14 and not more than 18 is used. Here, HLB means a Hydrophile-Lipophile Balance, which is the balance of hydrophilicity and lipophilicity of the emulsifier. The HLB value of the emulsifier used in the present invention is calculated by the Atlas method and by the following formula:

Theoretical HLB value=20×{1−(saponification value of ester/neutralization number of constituent fatty acid)} wherein the "saponification value of ester" is the amount (mg) of sodium hydroxide necessary for completely saponifying 1 g of polyglycerol fatty acid ester, and the "neutralization number of constituent fatty acid" is the amount (mg) of sodium hydroxide necessary for neutralizing 1 g of fatty acid constituting polyglycerol fatty acid ester. When an emulsifier having an HLB value, obtained from the above formula, of less than 14 or above 18 is used, an emulsified state and emulsion stability preferable as a preparation are difficult to achieve.

An emulsifier having certain properties of the above-mentioned (C) and usable in the present invention is, for example, an emulsifier showing a transmittance of 1 wt % aqueous solution at 600 nm of not less than 80%. The transmittance of the aqueous solution of the emulsifier can be obtained by measuring an absorbance at 600 nm by using a general spectrophotometer and calculating from the following formula:

absorbance=log(100/transmittance).

Preferable examples of the (C) emulsifier which comprises fatty acid monoester of polyglycerol having an average degree of polymerization of not less than 10, and an HLB value of not less than 14 and not more than 18 or a transmittance of 1 wt % aqueous solution at 600 nm of not less than 80%, wherein the content of polyglycerol having a degree of polymerization of not less than 6 is not less than 65 wt % in total or the content of linear polyglycerol and branched chain polyglycerol is not less than 60 wt % in total, include an emulsifier containing polyglycerol monooleate or monomyristate having an average degree of polymerization of not less than 10.

Moreover, as an emulsifier that can be encompassed in (C) emulsifier in the present invention, an emulsifier containing polyglycerol fatty acid monoester having an average degree of polymerization of not less than 10 as a primary composition, wherein the content of polyglycerol having a degree of polymerization of not less than 6 is not less than 65 wt % in total, and the total content percentage of linear polyglycerol and branched chain polyglycerol is less than 60 wt %, for example, emulsifier A (decaglyceryl monomyristate) can be mentioned. In addition, an emulsifier containing polyglycerol fatty acid monoester wherein the content of polyglycerol having a degree of polymerization of not less than 6 is not less than 75 wt % in total, the content of polyglycerol having a degree of polymerization of not less than 7 is not less than 60 wt % in total, the content of polyglycerol having a degree of polymerization of not less than 8 is not less than 50 wt % in total, and the total content percentage of linear polyglycerol and branched chain polyglycerol is less than 60 wt %, for example, emulsifier B (decaglyceryl monomyristate) can be mentioned. In addition, an emulsifier containing polyglycerol fatty acid monoester wherein the content of polyglycerol having a degree of polymerization of not less than 6 is not less than 75 wt % in total, the content of polyglycerol having a degree of polymerization of not less than 7 is not less than 60 wt % in total, the content of polyglycerol having a degree of polymerization of not less than 8 is not less than 50 wt % in total, and the content percentage of linear polyglycerol and branched chain polyglycerol is not less than 60 wt % in total, for example, emulsifier C (decaglyceryl monooleate, "Sunsoft AA", manufactured by Taiyo Kagaku Co., Ltd.), and emulsifier D (decaglyceryl monomyristate, "Sunsoft AB", manufactured by Taiyo Kagaku Co., Ltd.) can be mentioned. In addition, an emulsifier containing polyglycerol fatty acid monoester wherein the total content of polyglycerol having a degree of polymerization of not less than 6 is less than 65 wt % and the total content percentage of linear polyglycerol and branched chain polyglycerol is less than 60 wt %, for example, emulsifier E (decaglyceryl monomyristate) can be mentioned.

To prepare the emulsifying preparation of the present invention, the above-mentioned emulsifier of (C) is preferably contained within the range of 0.1 to 30 wt % of the total amount of the emulsifying preparation according to the properties and the amount of the oil phase and aqueous phase component. In the present invention, moreover, an emulsifier other than the above-mentioned polyglycerol fatty acid monoester having an average degree of polymerization of not less than 10 can also be contained as long as the characteristics of the present invention are not impaired.

The emulsifying preparation of the present invention can be prepared by a general method. For example, it is prepared by mixing aqueous phase components, dissolving the mixture by heating, gradually adding oil phase components previously mixed and dissolved by heating, and applying a mixing treatment using a homomixer, a colloid mill, a high-pressure homogenizer, a nanomizer, a microfluidizer, and the like for emulsification. Water-soluble components having low stability to heat are desirably dissolved separately in a small amount of water, emulsified therein, cooled and added, followed by mixing.

Other features of the invention will become apparent in the course of the following descriptions of exemplary embodiments which are given for illustration of the invention and are not intended to be limiting thereof.

EXAMPLES

Example 1

Emulsifying Preparation

| | | |
|---|---|---|
| (1) glycerol | 55.0 | (wt %) |
| (2) purified water | 3.0 | |
| (3) emulsifier C ("Sunsoft AA", manufactured by Taiyo Kagaku Co., Ltd.) | 6.0 | |
| (4) medium-chain triglyceride | 13.0 | |
| (5) sucrose acetate isobutyrate | 14.5 | |
| (6) dihydrocapsiate | 2.5 | |
| (7) ascorbic acid | 1.0 | |
| (8) purified water | 5.0 | |

Production method: (1) to (3) are mixed and dissolved by heating to 90 to 95° C. (4) to (6) mixed and dissolved by heating to 90 to 95° C. in advance are added thereto, and the mixture is mixed and emulsified in a TK homomixer. After cooling to 30° C., (7) dissolved in (8) is added and mixed therewith.

Comparative Examples 1-4

Emulsifying Preparation

In the above-mentioned Example 1, emulsifier C of (3) ("Sunsoft AA", manufactured by Taiyo Kagaku Co., Ltd.) was changed to "Decaglyn 1-O" (manufactured by Nikko Chemicals Co., Ltd.), "POLYALDO 10-1-0 KFG" (manufactured by Lonza), "RIKEMAL JV-0381" (manufactured by RIKEVITA), or "CAPROL PGE 860" (manufactured by ABITEC), and preparation was produced in the same manner.

The respective compositions and HLB values of the emulsifiers used in Example 1 and Comparative Examples 1-4 are shown in Table 3. In addition, the transmittances of 1 wt % aqueous solutions of the emulsifiers used in Example 1 and Comparative Examples 1-4 at 600 nm are compared in Table 4.

TABLE 3

| | emulsifier | composition | HLB value |
|---|---|---|---|
| Example 1 | emulsifier C (Sunsoft AA) (manufactured by Taiyo Kagaku Co., Ltd.) | decaglyceryl monooleate | 14.7 |
| Comparative Example 1 | Decaglyn 1-O (manufactured by Nikko Chemicals Co., Ltd.) | decaglyceryl monooleate | 13.8 |
| Comparative Example 2 | POLYALDO 10-1-0 KFG (manufactured by Lonza) | decaglyceryl monooleate | 12.2 |
| Comparative Example 3 | RIKEMAL JV-0381 (manufactured by RIKEVITA) | decaglyceryl monooleate | 12.5 |
| Comparative Example 4 | CAPROL PGE 860 (manufactured by ABITEC) | decaglyceryl oleate | 8.2 |

TABLE 4

| emulsifier | transmittance rate (%) |
|---|---|
| emulsifier C (Sunsoft AA) (manufactured by Taiyo Kagaku Co., Ltd.) | 82.0 |
| Decaglyn 1-O (manufactured by Nikko Chemicals Co., Ltd.) | 51.1 |
| POLYALDO 10-1-0 KFG (manufactured by Lonza) | 36.9 |
| RIKEMAL JV-0381 (manufactured by RIKEVITA) | 30.0 |
| CAPROL PGE 860 (manufactured by ABITEC) | 0.7 |

As is clear from Tables 3 and 4, of the emulsifiers used in Example 1 and respective Comparative Examples, only emulsifier C used in Example 1, which contains monooleate of decaglycerol as a primary composition, showed an HLB value within the range of not less than 14 and not more than 18, and only its 1 wt % aqueous solution showed a high transmittance exceeding 80% at 600 nm, which was 82.0%.

The emulsion particle sizes (median size) of the emulsifying preparations of Example 1 and Comparative Examples 1-4 after preparation were measured by a particle size distributor (LA-920, manufactured by Horiba, Ltd.) and the results are shown in Table 5.

TABLE 5

| sample | emulsion particle size (median size) (μm) |
|---|---|
| Example 1 | 0.26 |
| Comparative Example 1 | 0.27 |
| Comparative Example 2 | 0.32 |
| Comparative Example 3 | 0.23 |
| Comparative Example 4 | 5 |

When an emulsifying preparation is applied to pharmaceutical products and compositions for food, it is preferably produced to have an emulsion particle size (median size) of not more than about 0.5 μm, more preferably not more than about 0.25 μm, to ensure sufficient emulsion stability. Particularly, when the emulsion particle size exceeds 1 μm, emulsion destruction and the like easily occur. As is clear from Table 5, sufficiently small emulsion particles of 0.26 μm and 0.23 to 0.32 μm were produced in the emulsifying preparation of Example 1 of the present invention and the emulsifying preparations of Comparative Example 1 to 3. In contrast, it was evident that the emulsifying preparation of Comparative Example 4 using "CAPROL PGE 860" having a low HLB value as an emulsifier showed an emulsion particle size (median size) of not less than 5 μm and cannot secure emulsion stability for a long time.

Then, the emulsifying preparation of Example 1 that showed good emulsification stability during preparation and the emulsifying preparations of Comparative Examples 1-3 were evaluated for preservation stability at 5° C. For evaluation of the preservation stability, the emulsifying preparations of the Example and Comparative Examples as samples were preserved at 5° C., and the emulsion particle size (median size) was measured by a particle size distributor (manufactured by Horiba, Ltd., LA-920) over time and evaluated. The evaluation results are shown in FIG. 1.

As is clear from FIG. 1, in the emulsifying preparation of Example 1 of the present invention, and in the emulsifying preparation of Comparative Example 1 comprising decaglycerol monooleate as a primary composition and "Decaglyn 1-O" having an HLB value of 13.8 as an emulsifier, the median size of the emulsion particles was maintained almost the same during the preservation period, and good preservation stability was shown. In contrast, in the emulsifying preparations of Comparative Examples 2 and 3 comprising decaglycerol monooleate as a primary composition and "POLYALDO 10-1-0 KFG" and "RIKEMAL JV-0381" having HLB values of 12.2 and 12.5 and showing transmittance of 1 wt % aqueous solution of less than 80%, the median size increased over time and the emulsions became unstable.

Moreover, the emulsifying preparations of Example 1 and Comparative Example 1 that showed good preservation stability at 5° C. were evaluated for the preservation stability at 24° C. and 44° C. That is, the emulsifying preparations of Example 1 and Comparative Example 1 as samples were each preserved at 24° C. and 44° C., and the emulsion particle size (median size) of each sample was measured over time with a particle size distributor (manufactured by Horiba, Ltd., LA-920). The evaluation results are shown in Table 6.

TABLE 6

| sample | preservation temperature | number of days of preservation (days) | | |
|---|---|---|---|---|
| | | 0 | 15 | 60 |
| Example 1 | 24° C. | 0.27 | 0.31 | 0.36 |
| | 44° C. | 0.27 | 0.19 | 0.51 |
| Comparative Example 1 | 24° C. | 0.27 | 0.31 | 0.34 |
| | 44° C. | 0.27 | 0.67 | 1.30 |

As is clear from Table 6, the emulsifying preparation of Example 1 of the present invention did not show a time-course, clear increase in the median size of the emulsion particles at both 24° C. and 44° C., thus showing good preservation stability at both temperatures. In contrast, the emulsifying preparation of Comparative Example 1 comprising decaglycerol monooleate as the composition and "Decaglyn 1-O" showing an HLB value of 13.8 and transmittance of 1 wt % aqueous solution of 51.1% as an emulsifier did not show a clear median size increase at 24° C., but showed a time-course median size increase at 44° C., thus demonstrating that sufficient preservation stability cannot be achieved at 44° C. which corresponds to the temperature in a warehouse during the summer season.

As described above, the emulsifying preparation of Example 1 of the present invention showed emulsification stability and preservation stability sufficient as an emulsifying preparation for pharmaceutical products or foods.

Example 2

Emulsifying Preparation

| (1) hydrogenated starch syrup | 55.0 (wt %) |
|---|---|
| (2) purified water | 3.0 |
| (3) emulsifier A (decaglyceryl monomyristate) | 6.0 |
| (4) medium-chain triglyceride | 13.0 |
| (5) sucrose acetate isobutyrate | 14.5 |
| (6) dihydrocapsiate | 2.5 |
| (7) ascorbic acid | 1.0 |
| (8) purified water | 5.0 |

Production method: (1) to (3) are mixed and dissolved by heating to 90 to 95° C. (4) to (6) mixed and dissolved by heating to 90 to 95° C. in advance are added thereto, and the mixture is mixed and emulsified in a TK homomixer. After cooling to 30° C., (7) dissolved in (8) is added and mixed therewith.

Examples 3 to 6 and Comparative Example 5

Emulsifying Preparation

Preparations produced in the same manner as in the above-mentioned Example 2 except that emulsifier A of (3) was changed to emulsifier B (decaglyceryl monomyristate), emulsifier C ("Sunsoft AA", manufactured by Taiyo Kagaku Co., Ltd.), emulsifier D ("Sunsoft AB", manufactured by Taiyo Kagaku Co., Ltd.) and emulsifier E (decaglyceryl monomyristate) were used as Examples 3-6, respectively. In addition, a preparation produced in the same manner except that emulsifier was changed to the following emulsifier F was used as Comparative Example 5. Emulsifier F contains hexaglyceryl monolaurate, which is polyglycerol fatty acid monoester having an average degree of polymerization of less than 10, as a primary composition, and has an HLB value of 14.1. The compositions and HLB values of the emulsifiers used in Examples 2 to 6 and Comparative Example 5 are summarized in Table 7.

In addition, the degree of polymerization distribution of polyglycerol constituting the emulsifiers of Examples 2 to 6, and the ratio of polyglycerol having a chain (linear and branched chain) structure or a cyclic structure are shown in Tables 8 to 11. The degree of polymerization distribution of polyglycerol, and the ratio of the chain structure or cyclic structure were measured by high-speed liquid chromatography mass spectrometer (LC/MS) under the following conditions.

Analysis Conditions of LC/MS:
  ionization mode: APCI, negative
  measurement range: 90-2000
  column: TSK gel α-2500 (7.8×300 mm)
  temperature: 40° C.
  eluent: water/acetonitrile 7/3
  flow: 0.8 mL, 100 ppm
  analysis time: 20 minutes

TABLE 7

| emulsifier | composition | HLB value |
|---|---|---|
| A | decaglyceryl monomyristate | 14.8 |
| B | decaglyceryl monomyristate | 15.0 |
| C | decaglyceryl monooleate | 14.7 |
| D | decaglyceryl monomyristate | 15.9 |
| E | decaglyceryl monomyristate | 14.5 |
| F | hexaglyceryl monolaurate | 14.1 |

TABLE 8 constituent polyglycerol of emulsifier A/content (wt %)

degree of polymerization

| structure | 1 | 2 | 3 | 4 | 5 | 6 | 7 | 8 | 9 | 10 | 11 | 12 | 13 | 14 | 15 | 16 | total |
|---|---|---|---|---|---|---|---|---|---|---|---|---|---|---|---|---|---|
| chain | 1.5 | 2.2 | 2.9 | 4.4 | 5.1 | 8.6 | 7.9 | 7.5 | 5.2 | 4 | 3.1 | 1.3 | 0.4 | 0.1 | 0 | 0 | 54.2 |
| cyclic | 1 | 1.6 | 2.3 | 3.5 | 4.5 | 5.3 | 5.6 | 5 | 4.8 | 3.3 | 2.3 | 1.2 | 0.3 | 0.1 | 0 | 0 | 40.8 |
| unknown | | | | | | | | | | | | | | | | | 5 |

* In the Table, chain structure shows linear or branched chain structure.

TABLE 9 constituent polyglycerol of emulsifier B/content (wt %)

degree of polymerization

| structure | 1 | 2 | 3 | 4 | 5 | 6 | 7 | 8 | 9 | 10 | 11 | 12 | 13 | 14 | 15 | 16 | total |
|---|---|---|---|---|---|---|---|---|---|---|---|---|---|---|---|---|---|
| chain | 1 | 1.6 | 1.9 | 2.6 | 3.5 | 4.6 | 5.5 | 6.2 | 7 | 6.4 | 5.2 | 3.3 | 2.4 | 1.3 | 0.6 | 0.2 | 53.3 |
| cyclic | 0 | 0 | 0.8 | 1.3 | 2.6 | 3.7 | 4.1 | 5.7 | 6.4 | 5.4 | 4.5 | 3.1 | 2.1 | 1 | 0.3 | 0 | 41 |
| unknown | | | | | | | | | | | | | | | | | 5.7 |

* In the Table, chain structure shows linear or branched chain structure.

TABLE 10 constituent polyglycerol of emulsifiers C and D/content (wt %)

degree of polymerization

| structure | 1 | 2 | 3 | 4 | 5 | 6 | 7 | 8 | 9 | 10 | 11 | 12 | 13 | 14 | 15 | 16 | total |
|---|---|---|---|---|---|---|---|---|---|---|---|---|---|---|---|---|---|
| chain | 0.8 | 1.8 | 2.4 | 3.7 | 5.7 | 7.3 | 8.8 | 10.8 | 12 | 11.3 | 8.4 | 5.6 | 3.7 | 2 | 0.8 | 0.2 | 85.3 |
| cyclic | 0 | 0 | 0.2 | 0.3 | 0.4 | 0.6 | 0.8 | 1.1 | 1.1 | 1.1 | 1.1 | 0.8 | 0.7 | 0.3 | 0.1 | 0 | 8.6 |
| unknown | | | | | | | | | | | | | | | | | 6.1 |

* In the Table, chain structure shows linear or branched chain structure.

TABLE 11 constituent polyglycerol of emulsifier E/content (wt %)

degree of polymerization

| structure | 1 | 2 | 3 | 4 | 5 | 6 | 7 | 8 | 9 | 10 | 11 | 12 | 13 | 14 | 15 | 16 | total |
|---|---|---|---|---|---|---|---|---|---|---|---|---|---|---|---|---|---|
| chain | 2.1 | 3.5 | 4.7 | 6.3 | 7.3 | 6.3 | 6.1 | 4.9 | 4.3 | 3.7 | 2.3 | 1 | 0.2 | 0.1 | 0 | 0 | 52.8 |
| cyclic | 1.9 | 2.3 | 3.3 | 3.9 | 4.3 | 4.3 | 4.7 | 4.7 | 4.1 | 3.7 | 3.1 | 1.3 | 0.5 | 0.1 | 0 | 0 | 42.2 |
| unknown | | | | | | | | | | | | | | | | | 5 |

* In the Table, chain structure shows linear or branched chain structure.

As is clear from Tables 8 to 11, of the emulsifiers used in Examples 2 to 6, the polyglycerol constituting emulsifier A used in Example 2, which contained decaglycerol monomyristate as a primary composition, had a content of glycerol having a degree of polymerization of not less than 6 of about 66% in total, and a content of linear or branched chain polyglycerol of about 54%. The polyglycerol constituting emulsifier B used in Example 3, which contained decaglycerol monomyristate as a primary composition, had a content of glycerol having a degree of polymerization of not less than 6 of about 79% in total, a content of glycerol having a degree of polymerization of not less than 7 of about 71% in total, a content of glycerol having a degree of polymerization of not less than 8 of about 61% in total, and a content of linear or branched chain polyglycerol of about 53%. The polyglycerol constituting emulsifier C ("Sunsoft AA", manufactured by Taiyo Kagaku Co., Ltd.) used in Example 4, which contained decaglycerol monooleate as a primary composition, and emulsifier D ("Sunsoft AB", manufactured by Taiyo Kagaku Co., Ltd.) used in Example 5, which contained decaglycerol monomyristate as a primary composition, had a content of glycerol having a degree of polymerization of not less than 6 of about 79% in total, a content of glycerol having a degree of polymerization of not less than 7 of about 71% in total, a content of glycerol having a degree of polymerization of not less than 8 of about 61% in total, and a content of linear or branched chain polyglycerol of about 85%. The polyglycerol constituting emulsifier E used in Example 6, which contained decaglycerol monomyristate as a primary composition, had a content of glycerol having a degree of polymerization of not less than 6 of about 55% in total, and a content of linear or branched chain polyglycerol of about 53%.

The emulsifying preparations of Examples 2 to 6 and Comparative Example 5 were measured for the emulsion particle size (median size) immediately after preparation and after preservation at 5° C. for 6 months by a particle size distributor (manufactured by Particle Sizing systems, NICOMP380) and the results thereof are shown in Table 12.

TABLE 12

| | emulsion particle size (median size) (μm) | |
|---|---|---|
| sample | immediately after preparation | after preservation at 5° C. for 6 months |
| Example 2 | 0.65 | 0.82 |
| Example 3 | 0.41 | 0.49 |
| Example 4 | 0.24 | 0.25 |
| Example 5 | 0.23 | 0.24 |
| Example 6 | 0.81 | 0.99 |
| Comparative Example 5 | 38.00 | |

When an emulsifying preparation is applied to pharmaceutical products or foods, it is preferably produced to have an emulsion particle size (median size) of not more than about 0.5 μm, more preferably not more than about 0.25 μm, to ensure sufficient emulsification stability as mentioned above. When the emulsion particle size exceeds 1 μm, emulsion destruction and the like easily occur. As is clear from Table 12, in the emulsifying preparations of Examples 4 and 5 of the present invention, sufficiently small emulsion particles of 0.24 μm and 0.23 μm were produced. In the emulsifying preparation of Example 3, small emulsion particles of about 0.4 μm were produced. In the emulsifying preparations of Examples 2 and 6, somewhat larger particles of 0.65 μm and 0.81 μm, respectively, were produced. In contrast, in the emulsifying preparation of Comparative Example 5, the emulsion particle size immediately after preparation was considerably large (38 μm), thus suggesting its instability.

When preserved at 5° C. for a long time of 6 months, the emulsifying preparations of Examples 4 and 5 showed almost no changes in the emulsion particle size, and in the emulsifying preparation of Example 3, the changes of the emulsion particle size were of a level free of problems. In the emulsifying preparations of Examples 2 and 6, the emulsion particle size after preservation at 5° C. for 6 months was 0.82 μm and 0.99 μm, respectively, and not more than 1 μm, thus suggesting capability of maintaining emulsification stability. The emulsifying preparation of Comparative Example 5 showed poor stability from immediately after preparation, and was excluded from the evaluation target.

Successively, the emulsifying preparations of Examples 2% to 6 were evaluated for preservation stability at 24° C. and 44° C. That is, the emulsifying preparations of Example 2 to 6 were each preserved at 24° C. and 44° C., and the emulsion particle size (median size) of each sample was measured over time with a particle size distributor (manufactured by article Sizing systems, NICOMP380). The evaluation results are shown in Table 13 by median size (μm).

TABLE 13

| sample | preservation temperature | number of days of preservation (days) | | |
|---|---|---|---|---|
| | | 0 | 15 | 60 |
| Example 2 | 24° C. | 0.65 | 0.81 | 1.01 |
| | 44° C. | 0.65 | 0.99 | 1.57 |
| Example 3 | 24° C. | 0.41 | 0.51 | 0.58 |
| | 44° C. | 0.41 | 0.68 | 0.98 |
| Example 4 | 24° C. | 0.24 | 0.31 | 0.36 |
| | 44° C. | 0.24 | 0.19 | 0.51 |
| Example 5 | 24° C. | 0.23 | 0.29 | 0.32 |
| | 44° C. | 0.23 | 0.28 | 0.43 |
| Example 6 | 24° C. | 0.81 | 0.98 | 1.21 |
| | 44° C. | 0.81 | 1.52 | 2.35 |

As is clear from Table 13, when preserved at either 24° C. or 44° C., the emulsifying preparations of Examples 4 and 5 of the present invention showed no clear time-course changes in the median size thereof, thus showing a good preservation stability. In the emulsifying preparation of Example 3, the particle size increased somewhat when preserved at 44° C., but the increase was of a level free of problems. In the emulsifying preparations of Examples 2 and 6, the particle size increased when preserved at 44° C., thus suggesting failure to provide sufficient preservation stability under high temperature preservation.

As described above, the emulsifying preparations of Examples 3 to 5 of the present invention showed emulsification stability and preservation stability sufficient as an emulsifying preparation for pharmaceutical products or foods. It was found that the emulsifying preparations of Examples 2 and 6 can also maintain sufficient emulsification stability and preservation stability by preservation in a refrigerator.

Industrial Applicability

According to the present invention, an emulsifying preparation sensorily superior even when added to pharmaceutical products such as liquid and the like or foods such as drinks and the like, which shows good preservation stability for a long time, imposes less restriction for formulation or production, and is suitable for application of an oil-soluble component to an aqueous phase can be provided.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. An emulsifying preparation, comprising:
(A) an oil phase component, comprising at least one oil-soluble component;
(B) an aqueous phase component, comprising at least one polyol; and
(C) an emulsifier, comprising at least one polyglycerol fatty acid monoester having an HLB value of not less than 14 and not more than 18,
wherein, in any one of the at least one polyglycerol fatty acid monoester, the polyglycerol moiety has an average degree of polymerization of not less than 10, the polyglycerol moiety has a degree of polymerization such that the amount of polyglycerol having a degree of polymerization of 7 or above is not less than 60 wt %, based on the total weight of said emulsifier, (C), and the polyglycerol moiety comprises linear or branched chained polyglycerol in an amount not less than 60 wt %, based on the total weight of said emulsifier, (C),
wherein said at least one oil-soluble component comprises at least one capsinoid compound, and said oil phase component, (A), is included in an amount of 20 to 50 wt % based on the total weight of said emulsifying preparation.

2. An emulsifying preparation according to claim 1, which comprises said aqueous phase component, (B), in an amount of 20 to 79.9 wt % based on the total weight of said emulsifying preparation.

3. An emulsifying preparation according to claim 1, which comprises said emulsifier, (C), in an amount of 0.1 to 30 wt % based on the total weight of said emulsifying preparation.

4. An emulsifying preparation according to claim 1, wherein said emulsifier (C) comprises polyglycerol monooleate having an average degree of polymerization of not less than 10 or polyglycerol monomyristate having an average degree of polymerization of not less than 10.

5. An emulsifying preparation according to claim 1, wherein the polyglycerol moiety of said polyglycerol fatty acid monoester has a degree of polymerization such that the amount of polyglycerol having a degree of polymerization of not less than 8 is not less than 50 wt %, based on the total weight of said emulsifier, (C).

6. An emulsifying preparation according to claim 1, wherein the polyglycerol moiety of said polyglycerol fatty acid monoester comprises the linear or branched chained polyglycerol in an amount not less than 80 wt %, based on the total weight of said emulsifier, (C).

7. An emulsifying preparation according to claim 1, wherein said at least one oil-soluble component in said oil phase component, (A), comprises at least one capsinoid compound selected from the group consisting of capsiate, dihydrocapsiate, and nordihydrocapsiate.

8. An emulsifying preparation, comprising:
(A) an oil phase component, comprising at least one oil-soluble component;
(B) an aqueous phase component, comprising at least one polyol; and
(C) an emulsifier, comprising at least one polyglycerol fatty acid monoester having a transmittance in 1 wt % aqueous solution at 600 nm of not less than 80%,
wherein, in any of the at least one polyglycerol fatty acid monoester, the polyglycerol moiety has an average degree of polymerization of not less than 10, the polyglycerol moiety has a degree of polymerization such that the amount of polyglycerol having a degree of polymerization of 7 or above is not less than 60 wt %, based on the total weight of said emulsifier, (C), and the polyglycerol moiety comprises linear or branched chained polyglycerol in an amount not less than 60 wt %, based wherein said at least one oil-soluble component comprises at least one capsinoid compound, and said oil phase component, (A), is included in an amount of 20 to 50 wt % based on the total weight of said emulsifying preparation.

9. An emulsifying preparation according to claim 8, which comprises said aqueous phase component, (B), in an amount of 20 to 79.9 wt % based on the total weight of said emulsifying preparation.

10. An emulsifying preparation according to claim 8, which comprises said emulsifier, (C), in an amount of 0.1 to 30 wt % based on the total weight of said emulsifying preparation.

11. An emulsifying preparation according to claim 8, wherein said emulsifier (C) comprises polyglycerol monooleate having an average degree of polymerization of not less than 10 or polyglycerol monomyristate having an average degree of polymerization of not less than 10.

12. An emulsifying preparation according to claim 8, wherein the polyglycerol moiety of said polyglycerol fatty acid monoester has a degree of polymerization such that the amount of polyglycerol having a degree of polymerization of not less than 8 is not less than 50 wt %, based on the total weight of said emulsifier, (C).

13. An emulsifying preparation according to claim 8, wherein the polyglycerol moiety of said polyglycerol fatty acid monoester comprises the linear or branched chained polyglycerol in an amount not less than 80 wt %, based on the total weight of said emulsifier, (C).

14. An emulsifying preparation according to claim 8, wherein said at least one capsinoid compound comprises at least one selected from the group consisting of capsiate, dihydrocapsiate, and nordihydrocapsiate.

* * * * *